(12) United States Patent
Frankle

(10) Patent No.: US 6,724,898 B1
(45) Date of Patent: Apr. 20, 2004

(54) SPEECH RECOVERY DEVICE

(75) Inventor: Christen M. Frankle, Los Alamos, NM (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 488 days.

(21) Appl. No.: 09/691,231

(22) Filed: Oct. 19, 2000

(51) Int. Cl.$^7$ .................................................. A61F 2/20
(52) U.S. Cl. ............................... 381/70; 434/185; 623/9
(58) Field of Search ................................. 434/156, 185; 84/334, 402; 181/21, 22, 126, 128; 381/70; 623/9

(56) References Cited

U.S. PATENT DOCUMENTS 4,187,635 A * 2/1980 Deissler ........................ 84/402
5,507,648 A 4/1996 Knopf

* cited by examiner

*Primary Examiner*—Minsun Oh Harvey
(74) *Attorney, Agent, or Firm*—James C. Durkis; Gemma Morrison Bennett; Paul A. Gottlieb

(57) ABSTRACT

There is provided an apparatus and method for assisting speech recovery in people with inability to speak due to aphasia, apraxia or another condition with similar effect. A hollow, rigid, thin-walled tube with semi-circular or semi-elliptical cut out shapes at each open end is positioned such that one end mates with the throat/voice box area of the neck of the assistor and the other end mates with the throat/voice box area of the assisted. The speaking person (assistor) makes sounds that produce standing wave vibrations at the same frequency in the vocal cords of the assisted person. Driving the assisted person's vocal cords with the assisted person being able to hear the correct tone enables the assisted person to speak by simply amplifying the vibration of membranes in their throat.

7 Claims, 2 Drawing Sheets

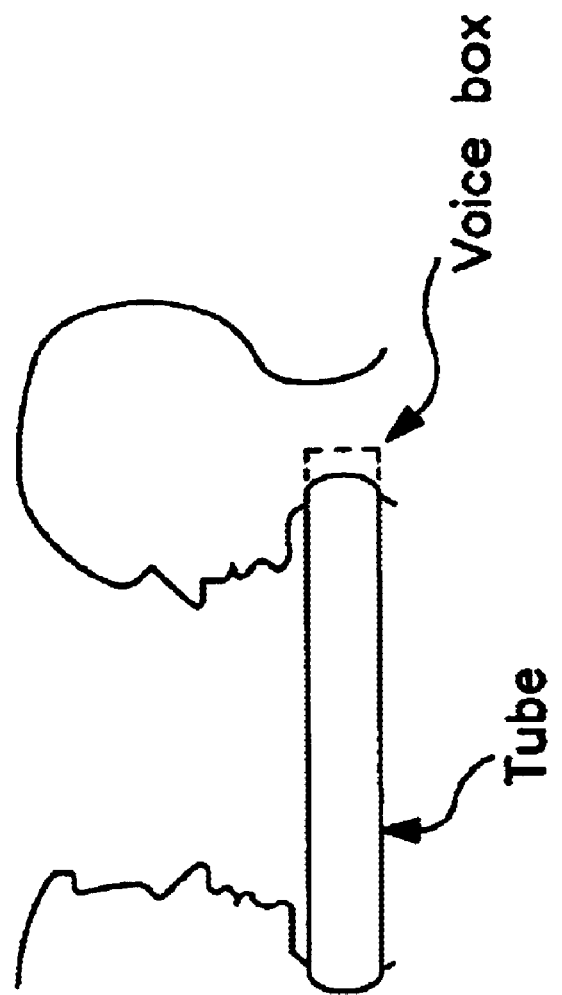

SPEECH RECOVERY DEVICE

This invention was made with government support under Contract No. W-7405ENG-36 awarded by the U.S. Department of Energy. The government has certain rights in the invention.

TECHNICAL FIELD

This invention relates to a device for speech recovery in aphasic patients.

BACKGROUND ART

Brain injured patients, most commonly those having suffered a stroke, may lose the ability to voluntarily or involuntarily speak or vocalize, even though their vocal cords may have physically recovered from any initial paralysis. Medically this condition may be part of a larger brain function impairment most commonly as part of conditions known as aphasia or apraxia, depending on the specific impairment or impairments. Once any physical paralysis has subsided, speech pathologists and therapists use a variety of techniques to induce a patient to speak again. One type of therapy involves physical stimulation, usually direct stimulation of the patient's throat area with a mechanical vibrator or the therapist's hand. Often these and other therapeutic approaches do not work.

For other types of speech impairments, other types of devices have been developed. There has been developed a tube type device to be applied to the lips of persons having speech impediments which cause an inability to sound out the "S", "Z", and "TH" sounds.

There is still a need for techniques and devices for assisting people with aphasia or apraxia in regaining speaking ability.

Therefore, it is an object of this invention to provide a method and device for assisting people with aphasia, apraxia or other conditions of similar effect to recover their speaking ability.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DISCLOSURE OF INVENTION

To achieve the foregoing and other objects, and in accordance with the purposes of the present invention, as embodied and broadly described herein, there has been invented an apparatus comprising: a hollow, rigid, thin-walled tube with semi-circular or semi-elliptical cut out shapes at each open end is positioned such that one end mates with the throat/voice box area of the neck of the assistor and the other end mates with the throat/voice box area of the assisted. The speaking person (assistor) makes sounds that produce standing wave vibrations in the vocal cords of the assisted person. Driving the assisted person's vocal cords with the assisted person being able to hear the correct tone enables the assisted person to speak by simply amplifying the induced vibration of membranes in their throat.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings:

FIG. 4 is a schematic drawing of how the ends of the invention device can be mated to the throats of the assistor and assistee.

BEST MODES FOR CARRYING OUT THE INVENTION

A hollow, relatively rigid, thin-walled tube is made of any material which will transmit the vibrations from the throat of a speaking person along the tube to the throat of an impaired speaker. More rigid materials are preferable because a tube of rigid material will absorb less of the vibrational energy being transmitted through the tube. Although other materials can be used successfully in the invention, cardboard, plastic and metal (including metal alloys) are presently preferred. Plastic is economical, readily available and easily handled. Certain plastics and stainless steel are good candidates for sterile medical environments.

Figure 1:
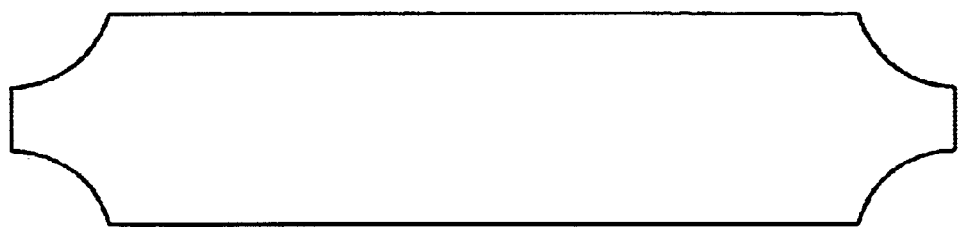
FIG. 1 is a schematic drawing of the side view of an invention device.
Figure 2:
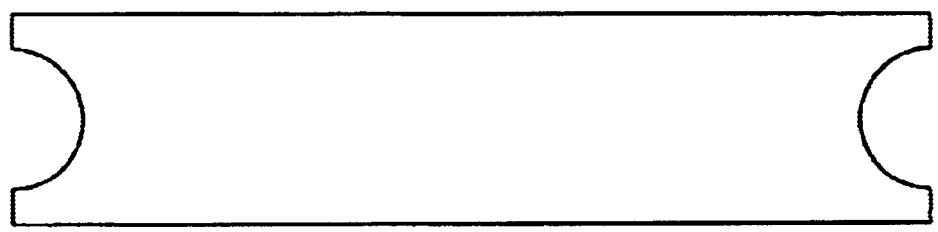
FIG. 2 is a schematic drawing of the top view of an invention device.
Figure 3:
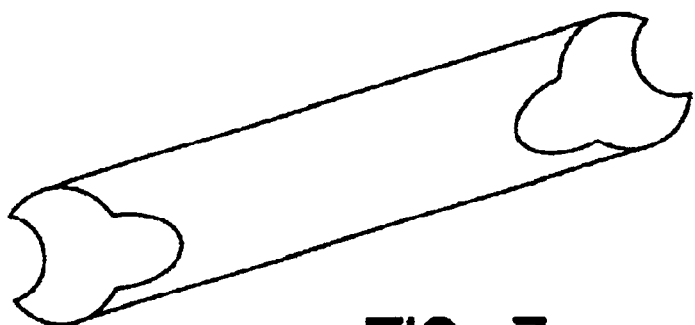
FIG. 3 is an isometric drawing of an invention device.

Each of the ends of the tube are cut away to provide an end surface that will mate comfortably and effectively with the frontal voice box area of each person's throat on the outside of the neck. Generally, semi-circular or semi-elliptical cutouts serve the purpose well. FIGS. 1, 2 and 3 show, respectively, the side view, top view and an isometric view of one convenient cutout shape that can be used to fit the ends of the speaking tube to the throat of the assistor or assistee as shown in FIG. 4.

The invention tubes need to be long enough for one end to be mated to the frontal voice box area of the neck of the speaking person (assistor) and the other end to be mated to the frontal voice box area of the neck of the person to be assisted (assistee) simultaneously with the people facing each other without forcing their faces into uncomfortable contact.

The lengths of the tubes preferably are selected to achieve an optimal frequency match for the assistor and assistee. The tube needs to be long enough to transmit a frequency low enough to be in a useful range and short enough to keep the transmitted energy from being too low. The fundamental wavelength of an open ended tube is twice the length of the tube. A longer tube will have a lower fundamental frequency and a shorter tube a higher fundamental frequency. Therefore, a somewhat longer tube may work better for an assistee with a deeper voice or a somewhat shorter tube may work better for an assistee with a higher pitched voice.

Generally, tubes from about 10 centimeters to about 40 centimeters are useful in the invention. Presently preferred are tubes in the range from about 15 centimeters to about 35 centimeters and presently more preferred are tubes in the range from about 20 to about 30 centimeters in length.

Whatever diameter can be conveniently cut to mate comfortably with a close touching fit with the throats of the assistor and assistee is useful in the practice of the invention. Generally, tubes with diameters in the range from about 2 cm to about 8 cm are useful in the invention. Presently preferred are tubes with diameters in the range from about 4 cm to about 6 cm. Tubes for children or adults with smaller necks will, of course, be smaller in diameter to achieve a good fit with the necks.

The walls of the tube are thick enough to make the tube readily self-supporting and thin enough to keep the weight in a reasonable range. Generally, tube walls in the range from about 0.5 mm to about 5 mm can be used in the invention. Tube walls in the range from about 1 mm to about 2 mm are generally preferred because this range provides a near-optimal strength-to-weight ratio for the tube.

A speech therapist who works with several patients having aphasia, apraxia or a condition having similar effects may want to have a set of several tubes with different dimensions to be able to match a frequency close to the frequency of their voices or to match a frequency somewhere in the range between the frequency of the assistor's and the assistee's voices. A speech therapy tube in accordance with the present invention might have a graduated diameter so that assistor and assistee having different sized necks could work well together. Similarly, a set of tubes of differing diameters, at least at one end, may be advantageous to a speech therapist in order to provide good matches to a variety of throat sizes.

Alternatively, the invention is a tube comprised of two tubes, one of which slides into the other in a manner similar to that in which extendable curtain rods are made so as to provide a way of adjusting the length of the tube suit the voice of the particular people involved in any particular therapy session.

One end of the tube is placed on the outside of the voice box area of the neck of the assistor; the other end of the tube is placed on the outside of the voice box area of the neck of the assistee. The speaking person begins by making single sounds, preferably starting with vowels. The effect of the voice box of the assistor is then that of a resonating cavity which, since it is coupled to the tube sets up standing waves in the tube. The frequency of the vibrations being transmitted is characteristic of the sounds being made by the speaking person (assistor). Because the tube is also coupled to the assistee's voice box, the assistee's vocal cords are driven to vibrate at the same frequency as the sound made by the assistor. Generally the tube will be vibrating in the range from about 100 Hz to about 10 kHz.

It is believed that the invention will work best if the assistor and the assistee have similar voice characteristics because if the voice pitch of the assistor were significantly higher or lower than that of the assistee, the assistee's vocal cords would not be driven at a frequency somewhat close to that at which the assistee's vocal cords would vibrate if the assistee were speaking. Selection of an appropriate length speech therapy tube can be used to compensate for at least some of the difference between the pitches of the voices of the assistor and assistee.

With the assistee's vocal cords being driven at the appropriate frequency and with the assistee also being able to hear the correct tone at the same, the assistee has simply to work to increase the amplitude of vibration of his or her membranes that are already vibrating at an appropriate frequency.

The following example will demonstrate the operability of the invention.

EXAMPLE 1

A speaking person closely related biologically to a person of the same gender who was unable to resume speaking as a result of damage from a stroke assisted the person who was unable to speak in regaining his ability to speak.

Semicircular shapes were cut out of the ends of a 25 cm long, 4 cm diameter tube so that the end surfaces of the tube fitted securely against the similar sized participants. The fundamental frequency of the tube was about 680 Hz.

Several times a day the assistor and assistee were positioned facing each other with the ends of the tube mated to the voice box area of the outside of their necks. Each trial period was carried out for about 15 to 20 minutes.

During each trial period the speaking assistor vocalized sounds with the tube in position between the necks of the assistor and assistee. The assistor started by vocalizing only a single vowel sound, then, as the sessions progressed, vocalized more vocal sounds. Once the assistee was able to vocalize vowel sounds, consonant sounds no longer required assistance from the assistor, probably because consonant sounds are far more dependent upon lip and tongue position than vocal cord movement.

The trial periods were continued several times a day for several days. As the trial periods continued, the assistee began incrementally regaining his speech, becoming able to vocalize more and more sounds on his own, until substantially complete ability to vocalize all sounds was achieved by the assistee.

While the apparatus and methods of this invention have been described in detail for the purpose of illustration, the inventive apparatus and methods are not to be construed as limited thereby. The claims of this patent are intended to cover all changes and modifications within the spirit and scope thereof.

INDUSTRIAL APPLICABILITY

The invention method and device can be used for assisting people with aphasia, apraxia or other conditions of similar effect to recover their speaking ability.

What is claimed is:

1. A method of assisting a person with aphasia, apraxia or other condition with similar effect to recover their speaking ability, said method comprising:

(a) pressing one end of a thin-walled hollow tube against the outside of the neck in the voice box area of the throat of a speaking person and simultaneously pressing the other end of said thin-walled hollow tube against the outside of the neck in the voice box area of the throat of said person with aphasia, apraxia or other condition with similar effect; and (b) said speaking person vocalizing sounds while said thin-walled hollow tube is pressed against the outside of the neck in the voice box area of the throat of said speaking person and pressed against the outside neck in the voice box area of the throat of said person with aphasia, apraxia or other condition with similar effect.

2. The method recited in claim 1 further comprising:

(c) said person with aphasia, apraxia or other condition with similar effect attempting to vocalize the same sounds vocalized by said speaking person simultaneously with said person vocalizing said sounds.

3. The method recited in claim 1 wherein said sounds are vowel sounds.

4. The method recited in claim 1 wherein said sounds are consonant sounds.

5. The method recited in claim 1 wherein said tube vibrates in the range from about 100 Hz to about 10 KHz.

6. The method recited in claim 1 wherein steps (a) and (b) are repeated.

7. The method recited in claim 2 wherein steps (a), (b) and (c) are repeated.

* * * * *